United States Patent [19]
Fischer et al.

[11] 3,933,612
[45] Jan. 20, 1976

[54] GLASS ELECTRODE STRUCTURE FOR RADIO CAPSULE

[75] Inventors: David J. Fischer, Corning, N.Y.; Hans J. Kunz; Thomas E. Norby, both of Raleigh, N.C.

[73] Assignee: Corning Glass Works, Corning, N.Y.

[22] Filed: May 13, 1974

[21] Appl. No.: 469,079

Related U.S. Application Data

[63] Continuation-in-part of Ser. No. 158,293, June 30, 1971, abandoned.

[52] U.S. Cl.......... 204/195 G; 204/286; 204/290 R; 128/2.1 A; 128/2.1 E
[51] Int. Cl.².................. G01N 27/36; A61B 5/04
[58] Field of Search...... 204/1 T, 195 G; 128/2.1 E, 128/2.1 A

[56] References Cited
UNITED STATES PATENTS

| | | | |
|---|---|---|---|
| 3,547,794 | 12/1970 | Nishimoto et al. | 204/195 G |
| 3,700,577 | 10/1972 | Grauer | 204/195 G |

FOREIGN PATENTS OR APPLICATIONS

| | | | |
|---|---|---|---|
| 1,237,808 | 3/1967 | Germany | 204/195 G |

OTHER PUBLICATIONS

"Handbook of Epoxy Resins," pp. 17–16, 1967.
Kitagawa et al, "Gastroenterology," Vol. 31, No. 3, Sept. 1966, pp. 368–372.
"Glass Electrode," Dole, 1941, p. 92.
Storer et al, "JAMA," Vol. 178, No. 8, pp. 134 & 135, Nov. 1961.

*Primary Examiner*—T. Tung
*Attorney, Agent, or Firm*—William J. Simmons, Jr.; Walter S. Zebrowski; Clarence R. Patty, Jr.

[57] ABSTRACT

Disclosed is a radio capsule having an electrode structure for measuring the concentration of an ionic species in an ion containing solution. A thin film conductive electrode is strongly bonded to the inner surface of a thin cylindrically shaped membrane of glass sensitive to the ionic species. A conductive lead wire makes electrical contact with the electrode. A mass of non-conductive reinforcing backing material having a thermal coefficient of expansion greater than that of the membrane strongly adheres to the conductive electrode and the membrane. The backing material is cured or solidified at a temperature sufficiently higher than that at which the electrode structure is to be used so that contraction of the backing material during curing places the membrane in a state of compression, thereby strengthening the same. The resultant electrode structure is incorporated into a radio capsule which also comprises circuitry for transmitting a signal modulated in accordance with the concentration of the measured ionic species.

13 Claims, 9 Drawing Figures

U.S. Patent   Jan. 20, 1976   3,933,612
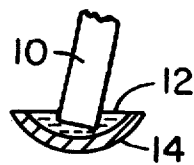
Fig. 1
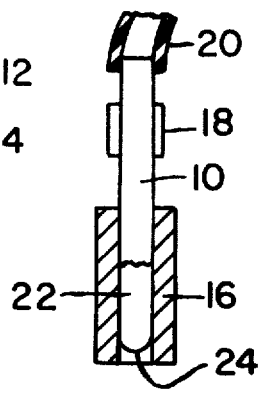
Fig. 2
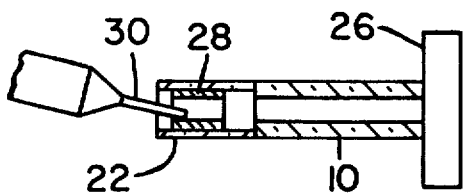
Fig. 3
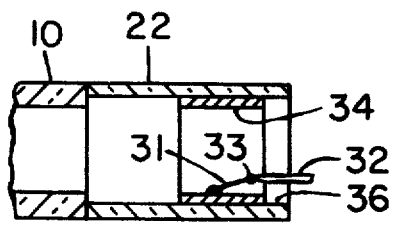
Fig. 4
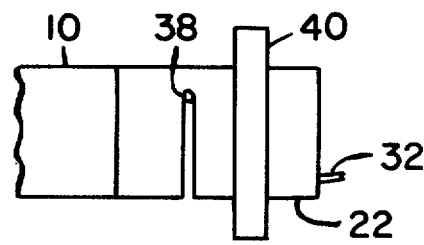
Fig. 5
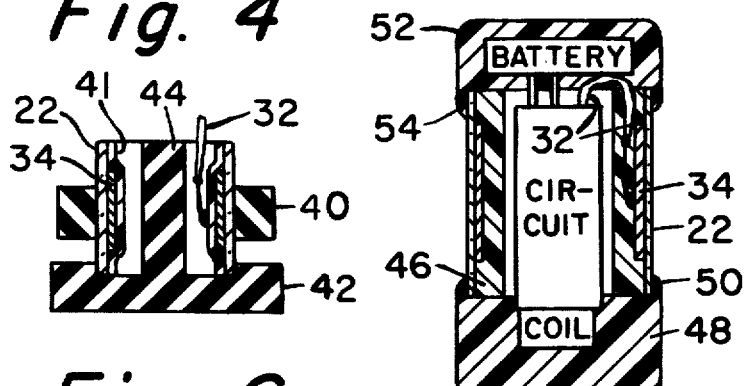
Fig. 6
Fig. 7
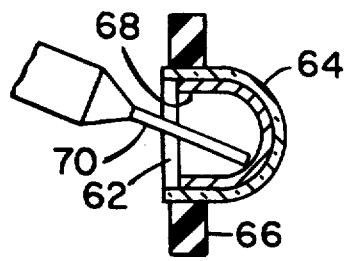
Fig. 8
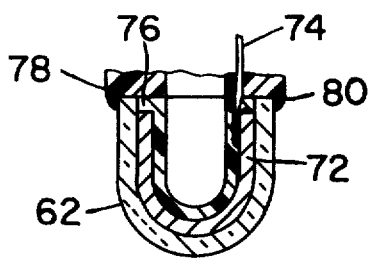
Fig. 9
INVENTORS.
David J. Fischer
Hans J. Kunz
Thomas E. Norby
BY
*William J. Simmons*
ATTORNEY

GLASS ELECTRODE STRUCTURE FOR RADIO CAPSULE

CROSS-REFERENCE TO RELATED APPLICATIONS

This application is a continuation-in-part of application Ser. No. 158,293, filed June 30, 1971, now abandoned, and is related to application Ser. No. 468,750 entitled "Reinforced Glass Electrode Structure" filed by us on May 10, 1974.

BACKGROUND OF THE INVENTION

This invention relates to solid, low impedance glass electrode structures for use in radio capsules used in the remote determination of ion activities.

The use of glass electrode structures for determining and measuring an ionic species in ionic solution is now common-place. In one usual form, the glass electrode structure comprises a tube made, at least in part, of an ion-sensitive glass. Glasses preferentially sensitive to hydrogen ion, potassium ion, sodium ion and the like are well known. The tube is sealed at one end to form an enclosure in which is disposed an electrolyte. The electrode structure also includes a conductive lead wire in contact with the electrolyte for picking up any potential at the electrolyte. When the tube exterior is in contact with a solution containing ions to which it is sensitive, a charge developes across the glass between the external solution and internal electrolyte in accordance with the ionic activity. The glass electrode structure in contact with the solution essentially constitutes a half cell.

The previously described glass electrode structure is normally employed with conventional pH equipment, the active ion sensing electrode structure being operatively connected to a standard half cell by means of high impedance, high gain electrometric amplification equipment. Such high impedance equipment is required to measure the potential of the ion sensing electrode structure since the resistivity of ion-sensitive glasses is about $10^{10}$ ohm-cm, even for so-called low resistance glasses which exhibit substantial ion sensitivity. Hence, the usual practice is to form the membrane of ion sensitive glass as a thin bulbous structure to reduce the impedance thereof. Even these electrodes may have an impedance of 100 megohms or more due to practical size limitations of the exposed sensing area.

While such electrode structures measure ion activity fairly rapidly and accurately, and are well adapted for continuous measurement, their usage poses several problems. Due to their inherent fragility arising out of the necessary thinness of the membrane, such electrodes are subject to breakage and failure. Furthermore, when attempts have been made to miniaturize this type of electrode the impedance thereof increases as the area of the ion sensitive membrane decreases, thereby placing an additional burden on the electrode and lead insulation and on the electrometric amplification equipment which must possess extremely high input impedance.

Attempts to provide stronger electrodes have resulted in relatively high impedance structures. U.S. Pat. No. 3,282,817 issued Nov. 1, 1966 to J. H. Riseman et al. discloses an ion-sensitive glass tube in which there is disposed the usual metallic, electrically conductive lead wire and a mass of solid, electrically conductive fused crystalline material in contact with both the lead wire and the ion-sensitive glass. This crystalline material may consist of a salt of silver or thallium. Electrodes of this type made with fused silver chloride, silver bromide, silver iodide or mixtures thereof are generally of high impedance, e.g., 100 to 1,000 megohms, the glass membrane accounting for only a small part of the total impedance. It appears that a very thin film of silver salt offers a high resistance in such a dry electrode structure and extremely small electrodes of this type cannot be used in application where low impedance is required.

In recent years attempts have been made to incorporate small ion-sensitive electrode structures in radio capsules small enough to be swallowed by a patient. Such electrode structures must be rugged and must provide a relatively low impedance output. Many of the techniques employed in normal laboratory monitoring of ion activities cannot be applied to radio capsules due to the small size thereof. The impedance of the aforementioned silver chloride filled electrode structure is too high to be conveniently used in a radio capsule. When well-known techniques have been applied in the development of radio capsule electrodes, inaccurate devices have resulted due to the simplicity of the circuitry, the low voltage and power available, and the requirement to insulate adequately in the small volume available in radio capsules. Compromises have been made by using low impedance metal-metal oxide or other types of pH sensors to simplify the circuitry problem. For example, U.S. Pat. No. 3,133,537 issued May 19, 1964 to H. Muth and U.S. Pat. No. 3,340,866 issued Sept. 12, 1967 to H. G. Noller disclose low impedance antimony electrodes used in conjunction with a pH measuring radio capsule. Although such electrodes are rugged and provide a low impedance output, they do not provide the accuracy which can be obtained from glass electrode structures.

Glass electrode structures having very thin liquid filled glass membranes have been considered for use in radio capsules, but the thin membrane is very easily broken during ordinary handling and represents a hazard to a patient who has swallowed such a capsule. Baskets made of corrosion resistant metal have been employed on some of these capsules to protect the fragile, ionsensing glass membrane. The protective basket restricts the flow of fluid over the membrane, thereby causing a response time lag and giving rise to the possibility that matter will be trapped by the basket and interfere with access of the electrode surface to the fluid under test.

SUMMARY OF THE INVENTION

An object of the present invention is to provide an improved ion-activity measuring electrode structure for use in radio capsules, said structure being characterized particularly by its low impedance and improved mechanical strength.

Briefly, the electrode structure of the present invention is of the type that is adapted to be used in a radio capsule for measuring the concentration of an ionic species in an ion containing solution. Such capsules generally comprise a housing in which is disposed an electrode structure for providing a voltage dependent on the activity of the ionic species in the solution. An oscillator circuit disposed in the housing generates an rf signal which is modulated by the voltage provided by the electrode structure. Means are provided for producing an operating voltage for the oscillator circuit and for providing a reference potential for the electrode structure. The electrode structure of the present invention is characterized in that it comprises a cylindrically shaped membrane of glass sensitive to the ionic species, said membrane having a thin film conductive electrode strongly bonded to at least a portion of the inner surface thereof. Conductive means are provided for connecting the oscillator circuit to the conductive electrode. To permit the use of extremely thin membranes, a mass of non-conductive backing material is strongly bonded to the inner surface of the conductive electrode and to that portion of the inner surface of the membrane adjacent to the conductive electrode. The thermal coefficient of expansion of the backing material is greater than that of the glass membrane, and the membrane is in a state of compression, thereby strengthening the electrode structure.

BRIEF DESCRIPTION OF THE DRAWINGS

FIGS. 1–6 illustrate basic steps in the construction of an electrode structure in accordance with the present invention. FIG. 1 shows the end of a hollow glass stem immersed in a pool of molten ion-sensitive glass. FIG. 2 shows apparatus for blowing a cylindrical membrane. FIG. 3 shows apparatus for applying a conductive electrode inside the cylindrical membrane. FIG. 4 shows a cross-sectional view of the membrane and stem after an electrical contact lead has been attached to the conductive electrode. FIG. 5 illustrates a method of severing the membrane from the stem. FIG. 6 shows a cross-sectional view of the membrane electrode composite in a mold.

FIG. 7 is a cross-sectional view of a schematic illustration of a radio capsule incorporating an electrode structure produced in accordance with the present invention.

FIG. 8 illustrates one of the steps in the construction of an alternative embodiment.

FIG. 9 is a cross-sectional view of an alternative embodiment of the present invention.

DETAILED DESCRIPTION

Electrode structures having small active surface areas, e.g. about 100 mm$^2$, and output impedances considerably less than 100 megohms are required for use in radio capsules. Electrode impedance should be low due to the limitations imposed on circuitry and insulation due to capsule size. Since the surface area of this type of electrode structure is very small, the ion-sensing glass membrane must be extremely thin and a good electrical connection must be made to the inner surface thereof to insure a low impedance output.

FIGS. 1–6 illustrate basic steps in the construction of a preferred low impedance ion-sensing electrode structure which is especially well suited for use in a radio capsule. The same reference numerals are used in several of these FIGURES to indicate identical parts. In FIG. 1 the end of a hollow glass stem 10 is immersed in a pool of molten ion-sensitive glass 12 which is disposed in a crucible 14. Stem 10 may consist of any type of glass that is suitable for supporting a thin walled cylinder which is to be formed on the end thereof. Molten glass 12 may consist of any suitable ion-sensitive glass composition such as the lithia pH glass described in U.S. Pat. No. 2,462,843 issued Mar. 1, 1949 to H. Cary et al. It could also consist of some other pH responsive glass composition such as one of those described in U.S. Pat. No. 2,497,235 issued Feb. 14, 1950 to G. A. Perley; U.S. Pat. No. 3,025,174 issued Mar. 13, 1962 to W. Simon; U.S. Pat. No. 2,668,143 issued Feb. 2, 1954 to P. T. Gilbert, Jr. et al.; or the like. A pNa responsive glass is described in U.S. Pat. No. 2,829,090 issued Apr. 1, 1958 to G. Eisenman et al. and a pK responsive glass is described in U.S. Pat. No. 3,041,252 issued June 26, 1962 to G. Eisenman et al. All of the aforementioned glasses are relatively low-resistivity glasses having resistive values in the order of $10^9$ to $10^{10}$ ohm-cm. In order to insure that the bond between the glass membrane and the stem remains temperature stable, the glass composition chosen for the stem 10 should have substantially the same thermal coefficient of expansion as the ion-sensitive glass over the temperature range in which the electrode structure is formed.

After a small gob of ion-sensitive glass has become adhered to the tip of stem 10, it is placed in a cylindrical carbon mold 16, the cross-section of which is shown in FIG. 2. A guide 18 aligns the stem glass properly in mold 16. An air line 20 is attached to the stem, and a cylindrical membrane 22 is blown. Although the thickness of membrane 22 is usually between 10 and 20 microns, it could be less than 10 microns. Depending on the particular glass used for the membrane, a minimum thickness will be reached below which the membrane is no longer useful for monitoring ion activity. Depending upon the type of ion-sensitive glass which is utilized, the electrode impedance is usually too high for use in radio capsules when the membrane thickness exceeds about 30 microns. The fragile membrane 22 is removed from mold 16 and is handled by the attached stem 10 while some of the subsequent steps are performed. To form the preferred electrode structure the tip 24 of membrane 22 is removed to permit the formation of a conductive layer on a portion of the inner surface of the membrane. Tip 24 may be severed by passing a hot platinum wire through the membrane to provide a smooth, fire-polished electrode end. The end of the cylindrical membrane may be flame-polished to give temporary added strength, and the system may also be flame-annealed to relieve unwanted stresses.

A thin, continuous, strongly bonded conductive film must be applied to at least a portion of the inner surface of the membrane 22. Whereas thermal reduction of metallic compounds produced a conductive film which bonded well to the glass membrane, vapor deposited and chemically reduced conductive films performed relatively poorly due to their poor adhesion to the glass. Perhaps the heating cycle to which the thermally deposited films were subjected formed an intermediate metal-glass layer which adhered well to the pure metal layer. The thermally reduced metallic layer can be formed by applying a coating of a solution of an organo-metal compound to the glass membrane and firing at an appropriate temperature. The organo-metal solution may be applied by any convenient method such as wash coating, brushing, spraying, or the like. When formed in accordance with the method of the present invention the metallic layer adheres well to the virgin surface of the glass, i.e., that surface which is initially formed when the membrane is blown. No surface roughening techniques such as grinding, etching or the like need be performed on the smooth virgin surface prior to forming the conductive film.

A particularly suitable method for applying a cylindrical coating of the solution to the inner surface of a small glass cylinder is illustrated in FIG. 3. Stem 10 is secured in a lathe chuck 26 which is rotated slowly while a layer 28 of organo-metal solution is applied to membrane 22 from a hypodermic needle 10. Stem 10 is the removed from chuck 26 and the membranestem composite is heated to at least 171°C in order to volatilize the organic constituents in the coating and to deposit a continuous, metallic silver film. In order to produce a strongly bonded silver film, the membrane should be heated to a higher temperature up to a maximum of about 870°C. In accordance with a preferred heat treatment cycle, the membrane is placed into a furnace, the temperature of which is about 300°C. The furnace temperature is then rapidly increased to about 550°C for at least 10 minutes to reduce the organo-metal solution and to provide a good bond between the resultant metal film and the membrane. The metal coated membrane can then be removed from the furnace, and the temperature thereof can be quickly reduced to room temperature. It was found that a continuous metallic film about one micron thick possessed the necessary properties for an ion-sensing electrode. Good electrodes were obtained by using an organo-silver compound known as Engelhard-Hanovia liquid organic silver No. 9374 which contains 18.0% silver and 0.15% rhodium. Other organo-metal solutions could be used to provide a conductive film of gold, tin, lead, platinum, palladium, nickel, cobalt, tantalum, chromium, cadmium, copper, vanadium or the like.

As shown in FIG. 4 an electrical contact lead is attached to the reduced conductive electrode 34. This electrical connection is preferably made by attaching a fine electrical contact lead 31 to electrode 34 by using another application of organo-metal compound at the point where lead 31 contacts the conductive electrode and firing for a time sufficient to form a metallic connection. A larger diameter lead 32 is then electrically connected to lead 31 by solder 33 or the like. The diameter of lead 32 should be at least twice that of fine lead 31, lead 31 consisting of 0.001 in. diameter silver wire and lead 32 consisting of 0.005 in. diameter silver wire in one embodiment. The fine wire lead 31 and solder connection 33 are so positioned that they will be completely covered with a non-conductive backing material to be applied in a subsequent step. Fine lead 31 can be easily and safely attached to electrode 34 by a small amount of silver, and the subsequent attachment of wire 32 and encasing thereof in backing material provides a fairly strong electrical lead extending from the resultant smooth cast surface.

A length of unsilvered ion-sensitive glass 36 is retained to provide improved insulation in the completed electrode structure. If the length of section 36 is greater than that required for the completed electrode structure, a portion thereof may be severed by using a hot platinum wire to give a smooth, fire-polished electrode end. Excess portions of membrane 22 have been removed by sawing and grit-blasting, but these methods may leave undesirable small cracks or stains in the glass.

The glass cylinders are washed in hot trichlorethylene, acetone, and alcohol and rinsed in flowing deionized water. After drying, a soft silicone washer 40 is placed over the membrane 22 in the vicinity of the conductive electrode 34 as shown in FIG. 5. A hot platinum wire is again used to cut the electrode structure to finished length, again leaving a length of membrane glass extending beyond the conductive electrode 34. Silicone washer 40 acts as a cushion and supports the fragile electrode structure as it is parted from the stronger stem 10. Washer 40 also serves as a place to grip the electrode structure for further processing.

At this point of the manufacturing process the electrode structure is extremely fragile. However, a solid structure which is much stronger than conventional liquid-filled electrodes can be made by providing the inner surface of the membrane-conductive electrode composite with a layer of a solid material such as glass, plastic or the like. Since a plastic such as epoxy provides a good seal, does not deleteriously affect the electroded membrane, and results in an extremely strong electrode structure, the use of this material is preferred. The inner surface and ends of the thin glass membrane-electrode assembly resulting from the severing step of FIG. 5 are treated with a 1% solution of silane to deposit a thin silane film 41 which enhances bonding of the reinforcing material. Dow Corning Z6040 silane, which was used for this process, is an epoxy functional material, glycidoxy-propyl trimethoxy silane. A chemical reaction results which forms a glass-epoxy bridging surface to prepare the glass for epoxy backing. The conductive electrode surface is also compatible with the silane solution, and a complete treated surface is prepared for the subsequent epoxy reinforcing step.

After the silane film is thoroughly dried the epoxy may be applied to the inner surface of the membrane and conductive electrode. To form a uniform layer of epoxy on the inner surface of the membrane 22 and electrode 34, the electroded membrane is placed on a silicone mold 42 having a core 44 projecting through the cylinder as shown in FIG. 6. An epoxy such as Hysol epoxy made with C9-4183 resin and H3840 hardener is cast between the glass membrane and the mold portion 44. This assembly is heated at an elevated temperature until the epoxy is cured. Since the thermal coefficient of expansion of the epoxy is about three or four times greater than that of the glass, the epoxy should be cured at a temperature sufficiently higher than the temperature at which the resultant electrode structure is to be used so that the shrinkage of the epoxy causes the glass membrane to be placed in a state of compression at use temperatures. This greatly increases the strength of the glass membrane and the overall electrode structure.

Optimum shrinkage properties for the above described epoxy were obtained by heating the epoxy at 60°C. for a period of time between 16 and 24 hours. Since the use temperature of a radio capsule to be swallowed by a human being is about 37°C, the glass membrane will never be weakened during use by going into tension. Prestressing the glass at an appropriate curing temperature above use temperature and providing a solid bond between the epoxy and both the membrane glass and conductive electrode in accordance with the aforementioned specific example resulted in a system which could withstand thermal shock up to 75°C for 0°C. Even though the glass may be less than 20 microns thick, it is sufficiently strong in this application because the compressive strength of the glass is the only property of interest at normal use temperatures. Thus, with a good bond between the epoxy and the membrane and conductive electrode, the composite electrode structure possesses almost as much mechanical strength as the solid epoxy backing alone. Electrode structures designed for use at temperatures up to 100°C were also formed in accordance with the above teachings. However, an unnecessarily high curing temperature causes very high compressive stress to exist in the electrode glass at use temperatures much lower than the curing temperature. Therefore, the curing temperature should be selected to give optimum electrode properties over the anticipated range of use temperatures.

FIG. 7 is a schematic illustration of a radio capsule incorporating a high strength electrode structure produced in accordance with the previously described method. For the sake of simplicity the silane film 41 is omitted from this FIGURE. The battery, oscillator circuit and antenna coil are illustrated in block diagram form since they are conventional, well-known radio capsule components. The battery may be constructed in accordance with the teachings of the aforementioned Muth and Noller patents, and these patents are accordingly incorporated herein by reference. These patents teach that one of the battery electrodes, which may be a silver-silver chloride electrode, may also function as the reference electrode of the ion-sensing arrangement. When such a dual function electrode is employed, the battery chamber is preferably connected to the exterior of the capsule by an aperture (not shown) which is sealed off by a semi-permeable membrane. The reference electrode for the ion-sensing arrangement could also be a separate component constructed in accordance with the teachings of U.S. Pat. No. 3,547,794 issued Dec. 15, 1970 to K. Nishimoto et. al.; however, this arrangement requires more space than a dual function electrode.

The hollow epoxy backing cylinder 46 may be formed by the mold shown in FIG. 6. The electrode structure including the epoxy backing can be tested as a discrete pH electrode to determine its potential response to pH solutions. The impedance and other properties of interest can also be determined before the electrode is incorporated into a radio capsule. A printed circuit oscillator having an antenna coil protruding from one end thereof is then disposed within the hollow epoxy cylinder, and this assembly is inserted into a silicone mold to form an epoxy end portion or cap 48 which slightly overlaps membrane 22 at portion 50. Still another silicone mold may be used to form a second end cap 52 in which the battery may be housed. End cap 52 also has an overlapping portion 54. The battery electrodes and the wire 32 are connected to the oscillator circuit prior to forming housing 52. Obviously, the battery is replaced in passive capsules by appropriate components for developing an induced charge.

The solid interior, ion-sensitive glass membrane electrode structure of the present invention maintained the accuracy of response of conventional liquid-filled laboratory electrode structures and yet had the low impedance and greater strength that are required for radio capsule use. The added advantages of rapid response to pH change and low preconditioning times were also obtained from this type of electrode construction. The high accuracy is obtained by using the same high quality ion-sensitive glass that is used in good laboratory electrodes. The low impedance is made possible by the use of very thin glass membranes and well adhering conductive electrodes which are strengthened by the solid, well bonded epoxy backing material. A low response time of less than one second, and a short solution preconditioning time are mainly the result of the low impedance and extreme thinness of the glass membrane. The impedance of cylindrical electrode structures having a diameter of about 0.3 in. and a length of about 0.3 in. was between 15 and 40 megohms. Conventionally made electrodes of similar size usually have an impedance between 100 and 500 megohms. A low resistivity lithia pH glass was utilized in the construction of an electrode structure of the type shown in FIG. 7. When immersed in a pH 7 test solution, this electrode structure showed a maximum variation of 5 millivolts in measuring a substantially constant potential of 100 millivolts to a silver-silver chloride reference electrode over a period of 18 hours while at a substantially constant temperature of 25°C.

A radio capsule electrode structure may have shapes other than that disclosed in the preferred embodiment. FIGS. 8 and 9 show an alternative embodiment which may be used. A cylindrically shaped membrane 62 having a spherical end portion 64 is formed as described hereinabove in conjunction with FIGS. 1 and 2. Instead of severing the spherical portion 64, a soft silicone washer 66 is placed over membrane 62 and that end of the membrane attached to the stem is severed leaving the membrane at the desired length. The membrane can be supported by washer 66 while a layer 68 of organo-metal solution is applied to the interior thereof. As described in connection with the preferred embodiment, the organo-metal solution may be applied by wash coating, brushing, spraying, or the like. As illustrated in FIG. 8, the preferred method of applying layer 68 is to insert a hypodermic needle 70 into the opened end of membrane 62 and apply the organo-metal solution while slowly rotating the membrane.

As described hereinabove, the layer 68 of organo-metal solution is heated in order to volatilize the organic constituents thereof and to deposit a continuous, metallic film electrode 72 which is strongly bonded to membrane 62. A lead wire 74 is attached to the reduced conductive electrode 72 as described in conjunction with FIG. 4. A thin layer of epoxy or other non-conductive backing material may be applied to the inner surface of membrane 62 and to the exposed surface of conductive electrode 72 by inserting a mold core into the open end of the membrane 62, applying a mixture of epoxy resin and hardener between the membrane and mold and thereafter curing the epoxy at the desired temperature. An alternative method of applying the thin layer 76 of epoxy is to coat the inner portion of the membrane and electrode with epoxy and continuously rotate the membrane during curing to achieve an even coating of epoxy. The electrode structure so formed can be incorporated into a radio capsule as one end thereof, the adjacent part 78 of the capsule housing including a portion 80 which overlaps the end of membrane 62. In such a capsule the circuitry could occupy the central portion thereof as illustrated in FIG. 7, and the transmitting coil could be disposed around the circuitry.

A radio capsule has been described herein as being capable of measuring hydrogen ion activity in the human ailmentary canal. Such capsules can also be used to determine specific ion activity in animals or inaminate objects such as chemical reaction or storage vessels, where the need to fully enclose the system for purposes of sterility or confinement of reaction products because of poisonous gas generation, presence of radio active materials, and the like, makes a wireless telemetry system advantageous.

We claim:

1. In a radio capsule for measuring concentration of an ionic species in an ion containing solution, said capsule being of the type comprising
   a housing,
   an electrode structure for providing a voltage dependent on the activity of said ionic species in said solution, said electrode structure being so disposed in said housing that a portion thereof is adapted to be exposed to said solution,
   an oscillator circuit for generating an rf signal which is modulated by the voltage provided by said electrode structure,
   means for providing an operating voltage for said oscillator circuit, and
   means for providing a reference potential for said electrode structure,
   said electrode structure being characterized in that it comprises
   a cylindrically shaped membrane of glass sensitive to said ionic species, said membrane having inner and outer surfaces, said outer surface of said membrane being adapted to be exposed to said solution,
   a thin film conductive electrode disposed on at least a portion of the inner surface of said membrane,
   conductive means for connecting said conductive electrode to said oscillator circuit, and
   a mass of non-conductive backing material adherent to the inner surface of said conductive electrode and to that portion of the inner surface of said membrane adjacent to said conductive electrode, the thermal coefficient of expansion of said backing material being greater than that of said glass membrane and said glass membrane being in a state of compression.

2. A radio capsule in accordance with claim 1 wherein said conductive means comprises a fine conductive wire in electrical contact with said conductive electrode.

3. A radio capsule in accordance with claim 2 wherein said conductive means further comprises a second wire electrically connected to said fine wire, the diameter of said second wire being at least twice that of said fine wire, said fine wire and the point of electrical connection of said fine and said second wires being encased in said mass of non-conductive material, said second wire projecting from said non-conductive material.

4. A radio capsule in accordance with claim 3 wherein said backing material is selected from the group consisting of plastic and glass.

5. A radio capsule in accordance with claim 4 wherein said backing material consists of epoxy.

6. A radio capsule in accordance with claim 5 wherein said conductive electrode consists of a material selected from the group consisting of silver, gold, platinum, palladium, tin, lead, nickel, cobalt, tantalum, chromium, cadmium, copper and vanadium.

7. A radio capsule in accordance with claim 6 wherein said housing comprises opposed end portions, said membrane being disposed centrally within said housing in such a manner that said end portions of said housing overlap corresponding end portions of said membrane.

8. A radio capsule in accordance with claim 6 wherein said glass membrane further comprises a spherically shaped end portion, said membrane being disposed at one end of said housing, the adjacent portion of said housing overlapping the corresponding portion of said membrane.

9. A radio capsule in accordance with claim 1 wherein the thickness of said membrane is less than 30 microns.

10. A radio capsule in accordance with claim 1 wherein the thickness of said membrane is between 10 and 20 microns.

11. A radio capsule in accordance with claim 1 further comprising a thin film of silane disposed between said non-conductive backing material and the adjacent portions of said electrode and said membrane, and wherein said backing material consists of epoxy and said electrode consists of silver.

12. A radio capsule in accordance with claim 1 wherein at least a portion of said oscillator circuit is disposed within said backing material.

13. A radio capsule in accordance with claim 1 wherein the surface of said membrane on which said conductive electrode is disposed is the smooth virgin surface.

* * * * *